(12) United States Patent
Tackett et al.

(10) Patent No.: US 7,851,175 B2
(45) Date of Patent: Dec. 14, 2010

(54) KIT FOR ASSAYING ACETYL TRANSFERASE OR DEACETYLASE ACTIVITY

(75) Inventors: Alan J. Tackett, Little Rock, AR (US); C. David Allis, New York, NY (US); Sean D. Taverna, Baltimore, MD (US)

(73) Assignees: The Board of Trustees of the University of Arkansas, Little Rock, AR (US); The Rockefeller University, New York, NY (US)

( * ) Notice: Subject to any disclaimer, the term of this patent is extended or adjusted under 35 U.S.C. 154(b) by 0 days.

(21) Appl. No.: 12/587,776

(22) Filed: Oct. 13, 2009

(65) Prior Publication Data

US 2010/0041085 A1 Feb. 18, 2010

Related U.S. Application Data

(62) Division of application No. 11/811,886, filed on Jun. 12, 2007, now Pat. No. 7,670,795.

(51) Int. Cl.
*C12Q 1/48* (2006.01)

(52) U.S. Cl. .......................... 435/15; 435/24; 435/975; 530/345

(58) Field of Classification Search ................ 435/15, 435/975

See application file for complete search history.

(56) References Cited

U.S. PATENT DOCUMENTS

| 7,670,795 | B2 * | 3/2010 | Tackett et al. ............... 435/15 |
| 2003/0224473 | A1 | 12/2003 | McCafferty |
| 2004/0091951 | A1 | 5/2004 | Schultz |
| 2006/0111287 | A1 | 5/2006 | Bianchi |

* cited by examiner

*Primary Examiner*—Ralph Gitomer
(74) *Attorney, Agent, or Firm*—Hugh McTavish

(57) ABSTRACT

The invention provides methods and kits for characterizing the activity of an acetyl transferase or deacetylase. The method involves enzymatically acetylating or deacetylating in vitro a substrate that is a peptide fragment of a full-length polypeptide, and then non-enzymatically acylating the peptide substrate with acyl groups that differ in molecular weight from the enzymatically added or removed acetyl groups. Typically, deuterated acetic anhydride is used to non-enzymatically acylate the substrate. The fully acylated substrate is then characterized by mass spectrometry to determine the amino acid positions of the substrate that are enzymatically acetylated or deacetylated.

9 Claims, 3 Drawing Sheets

SEQUENCE LISTING

<160> NUMBER OF SEQ ID NOS: 1

<210> SEQ ID NO 1
<211> LENGTH: 22
<212> TYPE: PRT
<213> ORGANISM: Homo sapiens

<400> SEQUENCE: 1

Ala Arg Thr Lys Gln Thr Ala Arg Lys Ser Thr Gly Gly Lys Ala Pro
1               5                   10                  15

Arg Lys Gln Leu Tyr Lys
            20

KIT FOR ASSAYING ACETYL TRANSFERASE OR DEACETYLASE ACTIVITY

This application claims priority under 35 U.S.C. §120 as a divisional application of U.S. patent application Ser. No. 11/811,886, filed Jun. 12, 2007 now U.S. Pat. No. 7,670,795.

BACKGROUND

The term "epigenetics" refers to modifications in gene expression that are controlled by heritable but potentially reversible changes in DNA methylation and/or chromatin structure. DNA is complexed with histone proteins to form the nucleosome subunits of chromatin. In the basic nucleosome structure, 147 base pairs of DNA are wrapped around an octamer of histone proteins H2A, H2B, H3, and H4. Histones are posttranslationally modified by methylation, acetylation, phosphorylation, and ubiquitination. And these posttranslational modifications have been shown to have regulatory effects on chromatin structure and gene transcription (Workman 2006). Thus, posttranslational modification of histones have epigenetic effects.

Acetylation of histones is accomplished by histone acetyltransferases (HATs). Deacetylation of histones is accomplished by histone deacetylases (HDACs). An imbalance of HAT and HDAC activity has been identified in some types of cancer cells (Grigani 1998, Lin 1998, Suzuki 2002). This causes alterations in the acetylation state of histones at certain locations in the chromosomes and changes in gene transcription (McLaughlin 2004).

HATs are a diverse set of enzymes. One subfamily of HATs is the Gcn5 N-acetyl transferases, including Gcn5, PCAF, Elp3, Hat1, Hpa2, and Nut1 (reviewed in Kimura 2005). Another family of HATs is the MYST HATs, including Morf, Ybf2, Sas2, and Tip60 (reviewed in Kimura 2005). Other HATs include p300/CBF and Taf1. The variety of HAT enzymes is further complicated by the fact that HATs reside in multiprotein complexes with other subunits, and changes in the subunit composition of a complex affect HAT activity and specificity.

Histone deacetylases are complex as well. Histone deacetylases are grouped into three classes based on homology with yeast deacetylases. Class I histone deacetylases include HDAC1, HDAC2, HDAC3 and HDAC8 and are homologous to yeast RPD3. Class II histone deacetylases have several members and are homologous with yeast Hda1. The third class of human histone deacetylases has seven members homologous to yeast Sir2 (Thiagalingam 2003)

Histone acetylation activates transcription and deacetylation silences genes, in general. (Berger 2002). Histone acetylation and other histone modification has been shown to regulate the activity of genes involved in tumorigenesis (Suzuki 2002; Glaser 2003).

The activity of HATs and HDACs varies depending on several factors, including the methylation state of the histone substrate, the amino acid residue in the histone being acetylated or deacetylated, and the chromosome position of the histones. (Cheung 2000, Qin 2006, Gilbert 2007, Lorincz 2001, Espada 2004)

With the emerging importance of histone acetylation and deacetylation in normal gene regulation and aberrant gene regulation in cancer and other diseases, improved tools to characterize the activity and specificity of enzymes catalyzing acetylation and deacetylation of histones and other proteins are needed.

SUMMARY

The invention involves methods and kit for characterizing the activity of an acetyl transferase or deacetylase or enzyme mixture containing an acetyltransferase or deacetylase. The methods involve enzymatically acetylating and/or deacetylating a peptide substrate that is a peptide fragment of a full-length polypeptide in vitro. Typically, this step adds or removes acetyl groups of natural isotope distribution. After enzymatically acetylating and/or deacetylating the peptide substrate, the peptide substrate is chemically fully acetylated with, e.g., deuterated acetic anhydride. This results in a peptide with enzymatically added or removed acetyl groups that have $H^1$ isotopic hydrogen and non-enzymatically added acetyl groups that differ in molecular mass because they are deuterated. Mass spectrometry is then used to determine the positions of amino acid residues in the peptide that are enzymatically acetylated or deacetylated. Preferably, the percent of peptides enzymatically acetylated or deacetylated at each amino acid residue is also determined. Kits for carrying out the methods are also provided.

Thus, one embodiment of the invention provides a method for characterizing the activity of an enzyme or enzyme mixture comprising an acetyl transferase or a deacetylase, the method involves first incubating the enzyme or enzyme mixture in vitro with a polypeptide substrate under conditions that allow acetylation and/or deacetylation of the polypeptide substrate to add acetyl groups to or remove acetyl groups from the polypeptide substrate to generate an enzymatically acetylated and/or deacetylated polypeptide, wherein the polypeptide substrate is a peptide fragment of a full-length protein. It involves as a second step reacting the enzymatically acetylated and/or deacetylated polypeptide with an acyl-containing substance that non-enzymatically reacts with the polypeptide to add acyl groups to the polypeptide to generate a fully acylated polypeptide; wherein the acyl group of the acyl-containing substance differs in molecular weight from the added or removed acetyl groups of the enzymatically acetylated and/or deacetylated protein or peptide. It involves as a third step subjecting the fully acylated polypeptide to mass spectrometry to determine amino acid positions of enzymatically added or removed acetyl groups on the polypeptide. Preferably this includes determining percent enzymatic acetylation or deacetylation at each of the amino acid positions of enzymatically added or removed acetyl groups.

Another embodiment of the invention provides a kit for characterizing the activity of an acyl transferase on a substrate, the kit comprising: (a) a polypeptide substrate for an acetyl transferase and/or a deacetylase, wherein the polypeptide substrate is a peptide fragment of a full-length protein; and (b) an acyl-containing substance that non-enzymatically reacts with the polypeptide substrate to add acyl groups to the polypeptide substrate to generate a fully acylated polypeptide; wherein the acyl group of the acyl-containing substance differs in molecular weight from a natural isotope composition acetyl group.

(B) Schematic representation of proteins identified in (A) as stable components of the Yng1-TAP-containing protein complex.

Figure 2:
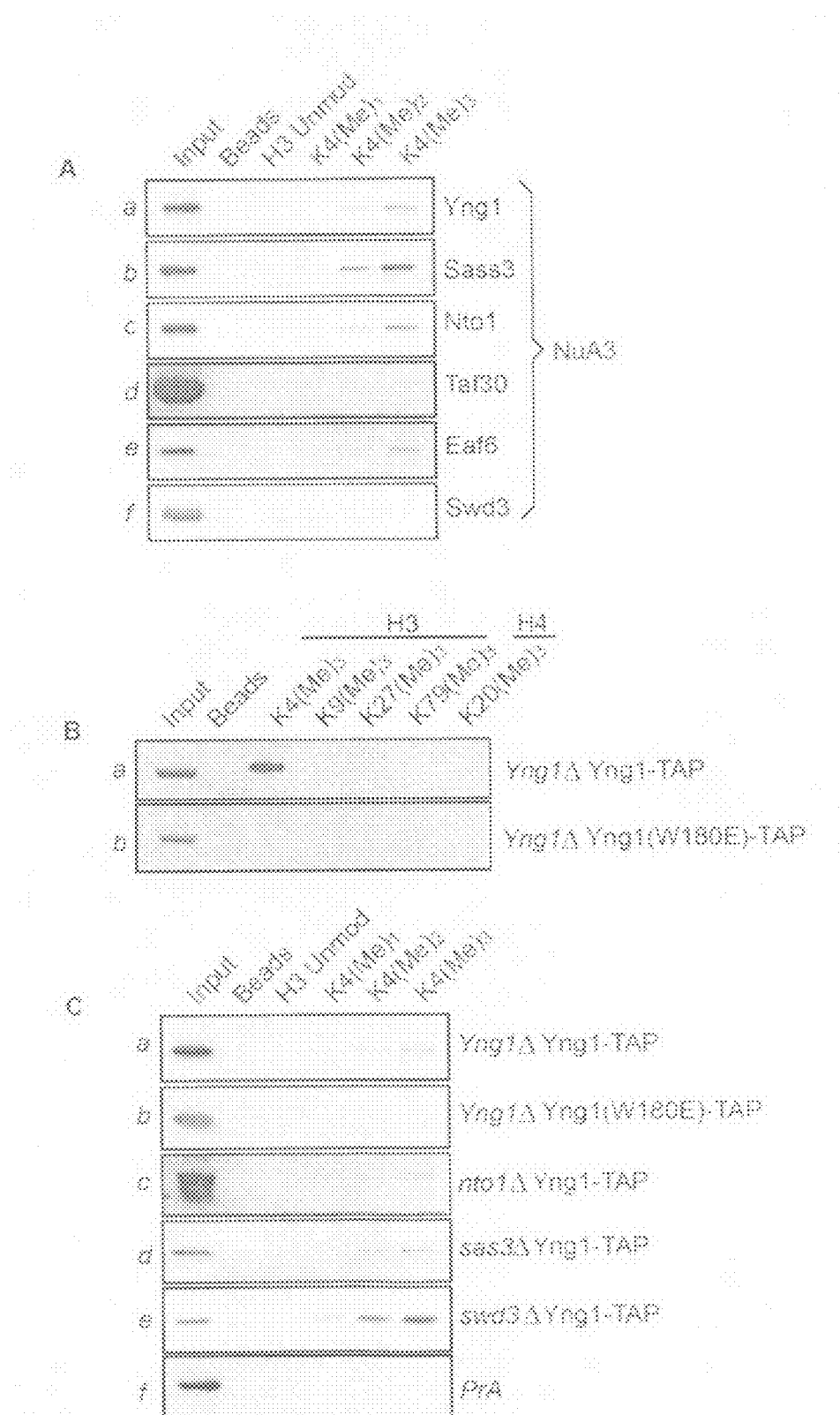

FIG. 2. NuA3 is Targeted to H3 K4me3 by Yng1

(A) SDS-PAGE of proteins isolated by peptide-pull-down assays. Peptide pull-down assays were performed by using yeast lysates from tagged strains and biotinylated H3 peptides (either unmodified, monomethylated, dimethylated, or trimethylated at K4) bound to streptavidin-linked Dynabeads. In all cases, pull-downs were analyzed with antibodies recognizing the PrA epitope in the TAP tag.

(B) NuA3 binding to H3K4me3 is context specific. Lysates from wild-type or Yng1 W180E strains were processed as in (A), and peptide pull-downs were performed with the H3K4me3 peptides indicated.

(C) The binding of NuA3 to H3K4me3 peptide is directed solely through the PHD finger of Yng1. Lysates from knockout strains indicated were processed and pull-downs were performed as in (A). The asterisk on (Cc) represents a breakdown product of the tagged Yng1.

Figure 3:
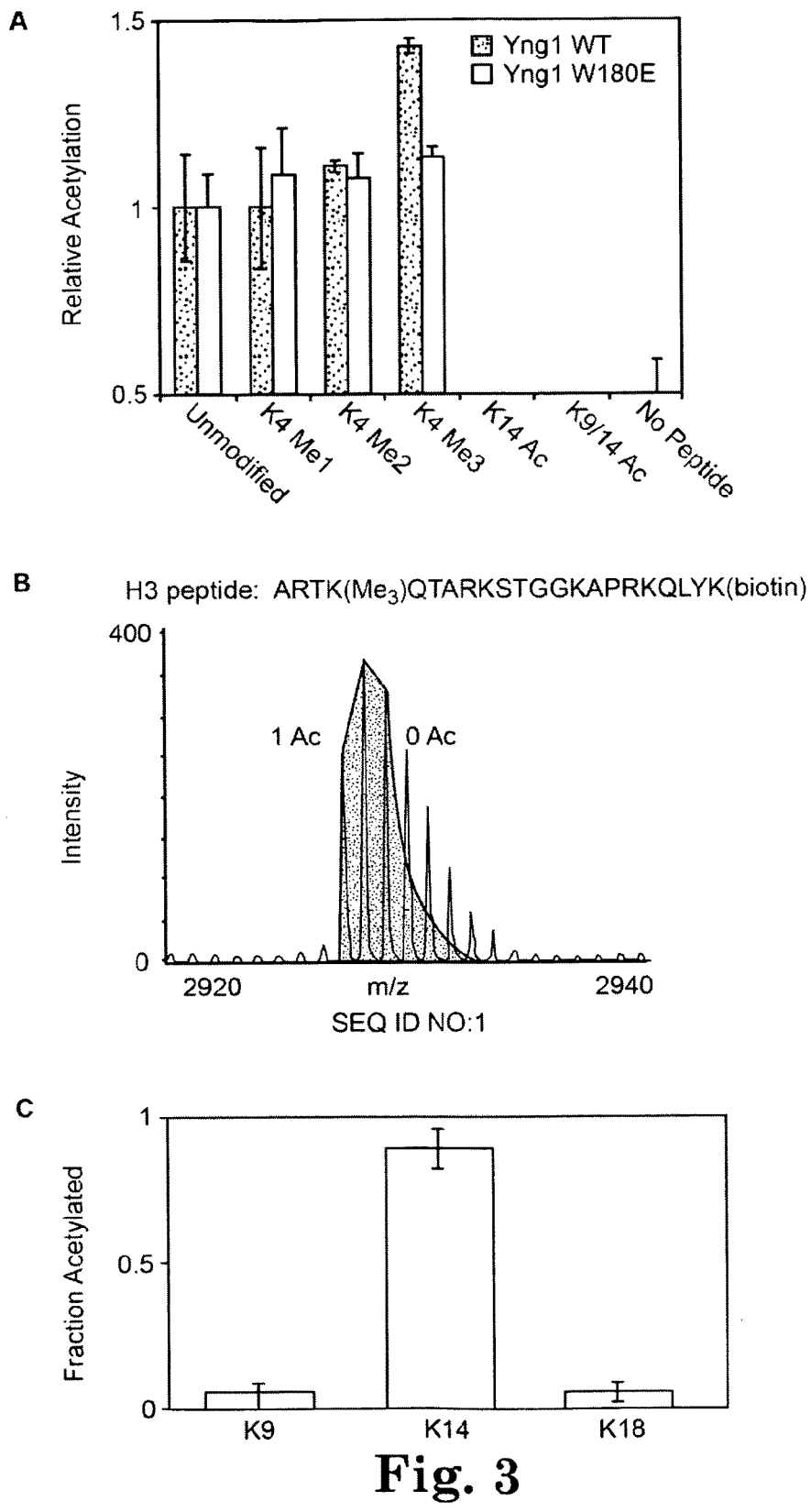

FIG. 3. HAT Activity of the Yng1-TAP-Containing Protein Complex (A) Bar graph of relative NuA3 acetylation activity on various substrates showing NuA3 exhibits enhanced HAT activity upon trimethylation of H3K4. Peptide-eluted Yng1-TAP-containing protein complex was incubated with differentially modified versions of histone H3 1-20 peptide and with radiolabeled acetyl CoA. Data were normalized to the amount of acetylation observed for the unmodified peptide.

(B) Mass spectrum of peptide from NuA3 acetylation reaction, showing that Yng1-TAP-containing NuA3 protein complex incorporated one acetyl group per peptide. Peptide-eluted Yng1-TAP containing NuA3 protein complex was incubated with H3K4me3 peptide and acetyl CoA. Following the HAT reaction, unacetylated lysines were chemically acetylated with d6-acetic anhydride. The mass spectrum from this reaction showed that only one acetylation was detectable on any given peptide. The shaded area shows the theoretical isotopic distribution from the singly acetylated H3 peptide. Peak area excluded from the shaded area is due to the unacetylated version of the H3 peptide.

(C) Plot of the fraction of acetylation at each modifiable lysine on the peptide. The peptide-eluted Yng1-TAP-containing NuA3 protein complex preferentially acetylated the input H3K4me3 peptide on K14. The fraction acetylated was determined by mass spectrometric fragmentation of the singly acetylated peptide from (B). Error bars are the standard deviation from triplicate analyses.

DETAILED DESCRIPTION

One embodiment of the invention involves a method of characterizing the activity of an enzyme or enzyme mixture comprising an acetyl transferase or a deacetylase on a polypeptide substrate. One utility of the invention is to determine the effect of posttranslational modifications, such as methylation or acetylation, of the substrate polypeptide on the activity of the acetyl transferase or deacetylase. The posttranslational modifications in some cases may alter the residues modified by the enzyme or the rate of catalysis.

Thus, in one embodiment, the polypeptide substrate is methylated.

In one embodiment, the method is executed with two or more polypeptide substrates differing in their methylation state but identical in their amino acid sequence and the activity of the enzyme or enzyme mixture on the two or more polypeptide substrates is compared. That is, step (a) comprises incubating the enzyme or enzyme mixture in vitro with two or more polypeptide substrates differing in their methylation state but identical in their amino acid sequence, and the method comprises comparing activity of the enzyme or enzyme mixture on the two or more polypeptide substrates.

The enzyme or enzyme mixture can be incubated in vitro with the two or more polypeptide substrates together or separately. Typically, the enzyme or enzyme mixture will be incubated with the two or more polypeptide substrates separately, but the enzyme or enzyme mixture can be incubated with the two or more polypeptide substrates together also. If incubated together, the two or more polypeptide substrates may be purified from each other before analysis by mass spectrometry. Alternatively, if the two or more polypeptide substrates can be distinguished in mass spectrometry, they may be analyzed together in mass spectrometry.

In another embodiment, step (a) comprises incubating the enzyme or enzyme mixture in vitro with two or more polypeptide substrates differing in post-translational modifications but identical in their amino acid sequence, and the method comprises comparing activity of the enzyme or enzyme mixture on the two or more polypeptide substrates.

In one embodiment, the two or more polypeptide substrates differ in their acetylation at one or more amino acid residues.

The activity and specificity of HATs, other acetyl transferases, histone deacetylases, and other deacetylases are affected by other post-translational modifications of the polypeptide substrates, such as phosphorylation, biotinylation, and ubiquitination. Thus, in some embodiments, the polypeptide substrate for in vitro acetylation and/or deacetylation is phosphorylated, biotinylated, and/or ubiquitinylated.

The polypeptide substrate is a peptide fragment of a full-length protein to facilitate mass spectrometric identification of the amino acid residues that are acetylated or deacetylated. Mass spectrometry currently works best to identify individual amino acids in peptides of approximately 40 residues or fewer. Thus, in one embodiment, the polypeptide substrate is a polypeptide of 40 residues or fewer. In particular embodiments, the polypeptide substrate is less than 60 amino acid residues, or less than 50, less than 40, or less than 30 amino acid residues.

In a preferred embodiment, the polypeptide substrate comprises a synthetic ligand and the method further involves before the mass spectrometry step, purifying the enzymatically acetylated and/or deacetylated polypeptide by contacting the polypeptide with a solid substrate coupled to a receptor for the ligand.

For instance, the ligand may be biotin, and the receptor may be avidin or streptavidin. The receptor may be immobilized to a bead, for instance. The ligand and receptor could be interchanged, so in another embodiment, the ligand could be avidin and the receptor immobilized to a solid substrate could be biotin. The terms "ligand" and "receptor" as used herein, mean two chemical entities that bind specifically to each other.

Another example of a synthetic ligand would be a poly-histidine sequence that is expressed by recombinant DNA means or chemically synthesized as a part of polypeptide substrate used in the methods and kits of the invention. A receptor for poly-histidine could be immobilized nickel.

Use of a polypeptide coupled to a synthetic ligand allows the polypeptide to be isolated from a reaction mixture easily. This facilitates mass spectrometry, since identification of the peptide fragments produced in mass spectrometry, and the amino acid positions that are acetylated or deacetylated, is much easier if the polypeptide sample is pure, i.e., has only a single polypeptide.

In the embodiments involving incubating the enzyme or enzyme mixture with two or more polypeptide substrates, the polypeptide substrates may have different ligands. This allows incubating the enzyme or enzyme mixture simultaneously with both or all of the two or more polypeptide substrates in the same incubation mixture, and then separating the two or more polypeptide substrates from each other by contacting the incubation mixture with separate receptors for each of the different ligands.

In one embodiment, the enzyme or enzyme mixture comprises an acetyl transferase, and step (a) comprises incubating the acetyl transferase in vitro with acetyl-CoA and the polypeptide substrate to generate an enzymatically acetylate polypeptide.

In another embodiment, the enzyme or enzyme mixture comprises a deacetylase, and step (a) comprises incubating the deacetylase in vitro with a partially or fully acetylated polypeptide substrate to generate an enzymatically deacetylated polypeptide. Class I and class II deacetylases do not require any cofactors, but class III deacetylases require nicotinamide. Thus, in some embodiments, the deacetylase is incubated in vitro with nicotanimade and the partially or fully acetylated polypeptide substrate.

To differentiate between the acetyl groups added or removed by enzymatic acetylation and/or deacetylation of the polypeptide and the non-enzymatically added acyl groups by mass spectrometry, the former and latter must differ in molecular weight. Preferably, the enzymatically added (or removed) acetyl groups and the non-enzymatically added acyl groups are chemically identical but differ isotopically. That way the proteins or peptides that are acetylated with either the enzymatically added acetyl groups or non-enzymatically added acetyl groups, since they are chemically identical, will fragment the same in mass spectrometry. This simplifies analysis of the mass spectrum.

The isotopic variation may be, for instance, $H^1$ versus deuterium or $C^{12}$ versus $C^{13}$. Preferably the enzymatically added (or removed) acetyl groups are of natural isotopic distribution. Thus, in a preferred embodiment the acetyl groups are $H^1$-acetyl (containing almost exclusively $H^1$ isotope hydrogen atoms), and the non-enzymatically added acyl groups are perdeuterated acetyl groups (containing 6 deuterium atoms).

It is also possible for the enzymatically added (or removed) acetyl groups to differ from the non-enzymatically added acyl groups chemically. For instance, the non-enzymatically added acyl groups might be formyl or propyl groups. Because the added or removed acyl groups differ chemically, polypeptides acetylated enzymatically may fragment slightly differently in mass spectrometry from the polypeptides acylated non-enzymatically, with, e.g., propyl or formyl groups. This would complicate the interpretation of the mass spectrum. But, the method could still work. Thus, in one embodiment the acetyl groups added or removed enzymatically and the non-enzymatically added acyl groups differ in size by one methyl group.

Preferably, the acyl-containing substance that non-enzymatically reacts with the polypeptide is an acyl anhydride. Preferably it is perdeuterated acetic anhydride. In another embodiment, the acyl-containing substance that non-enzymatically reacts with the protein or peptide is an acyl halide, e.g., perdeuterated acetyl chloride.

The acetyl transferase can be in one embodiment a histone acetyl transferase. Histone acetyl transferases (HATs) typically contain a catalytic subunit complexed with other polypeptides. The catalytic activity and substrate specificity of the various acetyl transferases varies depending on not only the catalytic subunit but also other subunits in the HAT complex. Different HATs, for instance, include a variety of chromatin binding domains, including bromodomains, chromodomains, WD40 repeats, Tudor domains, and PHD fingers that bind histone tails (Lee, K K 2007).

Thus, in one embodiment, the enzyme or enzyme mixture comprises a histone acetyl transferase and the polypeptide substrate is a peptide fragment of a histone.

In another embodiment, the enzyme or enzyme mixture comprises a deacetylase, and the polypeptide substrate is a peptide fragment of a histone.

In a preferred embodiment, the polypeptide substrate is enzymatically acetylated and/or deacetylated on lysine residues.

In one embodiment, the enzymatically acetylated and/or deacetylated protein or peptide is enzymatically acetylated and/or deacetylated on lysine residues and the acyl-containing substance that non-enzymatically reacts with the protein or peptide substrate to add acyl groups to the protein or peptide adds acyl groups to lysine residues.

In one embodiment, the polypeptide substrate is enzymatically acetylated and/or deacetylated on two or more amino acid residues. Patterns of acetylation at multiple residues in a polypeptide can be determined by tandem mass spectrometry as described in (Smith 2003), which is incorporated by reference.

In specific embodiments of the kit, the polypeptide substrate is a fragment of a full-length histone.

In particular embodiments, the acyl-containing substance that non-enzymatically reacts with the polypeptide substrate is deuterated acetic anhydride.

In particular embodiments, the polypeptide substrate comprises a synthetic ligand and the kit further comprises a solid substrate coupled to the receptor for the ligand.

In particular embodiments, the polypeptide substrate is methylated or acetylated or both.

In particular embodiments, the kit contains two or more polypeptide substrates that differ in post-translational modifications but are identical in their amino acid sequence.

In particular embodiments, the kit contains acetyl-coenzyme A.

In some embodiments, the kit contains nicotinamide.

In particular embodiments of the kit, the polypeptide substrate is a substrate for acetylation and/or deacetylation by the acetyl transferase or deacetylase at two or more amino acid residues.

The invention will now be illustrated by the following example. The example is intended to illustrate the invention but not limit its scope.

Example

Introduction

In eukaryotes, DNA is complexed with histone proteins to form the nucleosomal subunits of chromatin, the context in which nuclear factors differentially interpret the genome. A wealth of histone posttranslational modifications (PTMs), including methylation, acetylation, phosphorylation, and ubiquitination, have been identified whose functional effects are under active investigation. Specific histone PTMs may contribute to a "histone/epigenetic code" that dictates distinct biological outputs such as transcription, silencing, and DNA repair (Jenuwein and Allis, 2001, Strahl and Allis, 2000 and Turner, 2000). For example, methylation of K9 and K27 on histone H3 is often associated with heterochromatin, whereas K4 methylation is largely associated with euchromatin.

Many protein motifs characteristically associated with chromatin have recently been shown to have affinity for modified histone tails, acting as "effectors" for histone PTMs, notably lysine methylation. Chromodomains, for example, are often found in subunits of silencing complexes, providing a mechanism to bind to H3 methylated at K9 and/or K27 (lysine 9 and/or lysine 27). In keeping, modules such as chromodomains transduce specific PTM signals into changes in local chromatin structure, thereby limiting the accessibility to the underlying DNA (Khorasanizadeh, 2004). This chromodomain recruitment served to establish a useful paradigm wherein modules bind PTMs on histones, allowing distinct chromatin-associated enzymatic machineries to properly engage the chromatin fiber at discrete regions.

In contrast to the silencing paradigm with K9 and K27 methylation, chromatin immunoprecipitation (ChIP) experiments have consistently localized histone H3K4 trimethylation (hereafter H3K4me3) and H3/H4 hyperacetylation to promoter and 5' regions of transcriptionally active genes (Ng et al., 2003, Santos-Rosa et al., 2002 and Schneider et al., 2004). Furthermore, "ChIP-Chip" approaches that combine immunoprecipitation of chromatin-associated proteins with DNA microarray analysis have permitted generation of histone PTM "maps" along vast stretches of the *S. cerevisiae* genome that reinforce the correlation between K4 methylation, H3 hyperacetylation, and transcription as a global phenomenon (Pokholok et al. 2005 and references within). The spatial and temporal confinement of H3K4me3 and hyperacetylation along the genome strongly suggests that these PTMs participate in pathways involved in recruitment of general transcription factors or other elongation machinery.

The yeast orthologs of the PHD finger (plant homeodomain)-containing ING tumor suppressor family, Yng1, Yng2, and Pho23 (Loewith et al., 2000 and Bienz, 2006), have been shown to bind K4-trimethylated peptides with low µM affinity (Pena et al., 2006). Interestingly, Yng1 is a member of the NuA3 complex, one of four known multiprotein H3 HAT complexes (NuA3, ADA, SAGA, and SLIK/SALSA) that have been isolated from yeast (Eberharter et al., 1998, Grant et al., 1997, Sterner et al., 2002 and Howe et al., 2002). Although NuA3 has been implicated in transcriptional elongation through the interaction of Sas3, the MYST family member of NuA3 that serves as the HAT activity, with the FACT component Spt16 (John et al., 2000), the genome-wide binding pattern of NuA3 along chromatin has not been reported.

Removal of Yng1 from NuA3 reduces NuA3 H3 HAT activity on chromatin (Howe et al., 2002). However, the Yng1 PHD finger has not been directly linked to HAT activity in in vitro or in vivo assays. Thus, the functional contribution of the Yng1 PHD finger to H3K4me3 remains uncharacterized. Furthermore, since prior NuA3 functional assays were performed without regard for the methylation status of H3K4, any connections between K4 methylation, NuA3-dependent H3 acetylation, and the events surrounding transcription remain ambiguous. To better understand if H3K4me3 and hyperacetylation at the promoter (and 5' regions) are coupled by NuA3 HAT targeting through the Yng1 PHD finger, we undertook studies aimed at characterizing the Yng1 PHD-H3K4me3 interaction and describing the functional significance and genomic localization of the associated NuA3 HAT complex. Here, we provide genetic, biochemical, and biophysical evidence (including ChIP-Chip analysis) that Yng1 mediates NuA3-dependent H3K14 acetylation through a specific interaction between the Yng1 PHD finger and H3K4me3. Our studies are consistent with the general view that a hierarchical sequence of posttranslational histone modifications occurs at a promoter during the events that lead to transcriptional activation.

Methods

Yng1 was expressed as a TAP-tagged protein in yeast from a genomically TAP-tagged gene. The tandem affinity purification (TAP) tag consists of two immunoglobulin-binding domains of protein A from *Staphylococcus aureus* (zz-tag), a cleavage site for the tobacco etch virus (TEV) protease, and the calmodulin-binding peptide (CBP). (Rigaut 1999, Puig 2001). The TAP tag is added to the C-terminus of the protein by insertion at the 3'-terminus of the native open reading frame by homologous recombination. This ensures native expression levels. This strain was purchased from Open Biosystems (Huntsville, Ala., www.openbiosystems.com). Yeast cells were broken, and complexes containing Yng were isolated by affinity interaction with Dynabeads (Dynal) crosslinked to rabbit IgG (Cappel) as described in (Tacket 2005a).

Mass Spectrometry m/z values were determined on a MALDI-prOTOF (PerkinElmer Sciex) mass spectrometer. CID-based tandem MS analysis was performed with a MALDI-LTQ MS (Thermo Scientific). Monoisotopic peak areas were used to quantify the relative amount of light and heavy labeled peptide.

Results

Isolation and Characterization of the Yng1-Containing NuA3 HAT Complex

To verify that Sas3 and Taf30 are present in the purified NuA3 HAT complex and to identify additional stable components, we employed the recently described isotopic differentiation of interactions as random or targeted (I-DIRT) technology (Tackett et al., 2005b). TAP-tagged Yng1 was used to specifically isolate NuA3, keeping in mind that Sas3, its catalytic HAT subunit, has recently been associated with complexes found at boundary elements (Tackett et al., 2005a), and Taf30, another NuA3 component, has been shown to interact with TFIID, TFIIF, INO80, and RSC (Kabani et al., 2005). We isolated genomically TAP-tagged Yng1 under conditions that preserve in vivo protein interactions (Tackett et al., 2005a and Tackett et al., 2005b); in all cases, only the protein A (PrA) component of the TAP tag was utilized for purification. We believe that our extraction conditions maintained the integrity of the Yng1-containing complex because gel filtration analysis revealed a protein complex of similar size to that previously reported for NuA3 (John et al., 2000).

Figure 1:
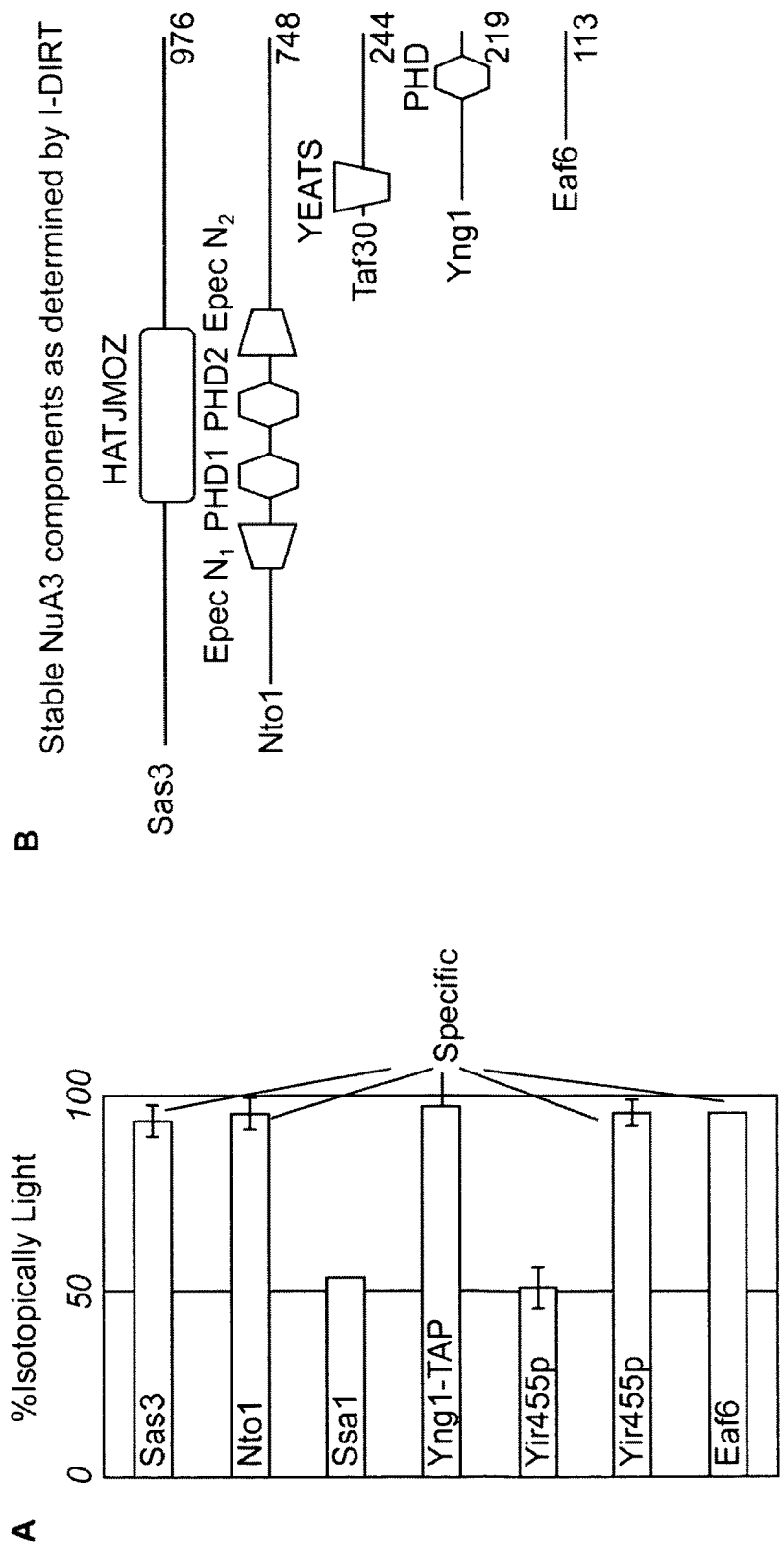
FIG. 1. Isolation of an Yng1-Containing NuA3 Protein Complex (A) I-DIRT analysis of the Yng1-TAP-associated proteins identified by SDS-PAGE. IgG-coated Dynabeads were incubated with *S. cerevisiae* lysate from either a strain containing no affinity tag or a strain containing TAP-tagged Yng1. The Yng1-TAP lysate contained an equal amount of d4-lysinelabeled cell lysate (untagged) for I-DIRT analysis. Yng1-TAP and associating proteins were resolved by 4%-12% denaturing gel electrophoresis, visualized by Coomassie staining, and excised for mass spectrometric protein identification. Proteins associated with an in-genome mutated version of Yng1 (W180E) were also identified (see text for details). Proteins identified as containing near 100% h4-lysine (isotopically light) are true protein complex components, while protein identifications containing 50% h4-lysine (and therefore 50% d4-lysine) are contaminants. Error bars show the standard deviation for lysine-containing peptides.

Briefly, tagged YNG1 cells, grown in isotopically light media, and wild-type (untagged) cells, grown in heavy isotopic (d4-lysine) media, were mixed in a 1:1 ratio by cell weight and co-lysed under cryogenic conditions. Proteins purifying with tagged Yng1 on IgG-Dynal beads were resolved by SDS-PAGE, visualized by Coomassie staining, and subjected to mass spectrometric protein identification (FIG. 1A). This analysis allowed identification of proteins that were either stably associated (peptides yielding an exclusively light labeled signature) or nonstably associated (1:1 ratio of light to heavy labeled peptides) with tagged Yng1 (Tacket 2005b). No significant enrichment of yeast proteins was identified in a mock purification from a yeast strain without an affinity tag (data not shown).

We inferred from the I-DIRT analysis that the stable NuA3 complex contains five proteins: Sas3 (98 kDa), Nto1 (86 kDa), Taf30 (27 kDa), Yng1 (25 kDa), and Eaf6 (13 kDa) (FIG. 1A); a schematic cartoon of these subunits and their known domains is represented in FIG. 1B. Nto1 and Eaf6 have not been previously published as members of the yeast NuA3 complex, and Eaf6 is also a stable member of the H2A/H4 NuA4 HAT complex (Doyon et al., 2004). The mammalian homologs of Nto1 (Jade 1/2/3 and BRPF 1/2/3) and Eaf6 (hEaf6) were recently shown to be in two HAT complexes containing ING 4/5 (H4-specific HBO1 HAT) and ING5 (H3-specific MOZ/MORF HAT) (Doyon et al., 2006). Interestingly, Nto1 has two PHD fingers surrounded by an interrupted Epc-N domain that is predicted to fold into a bromodomain-like α-helical structure with potential acetyllysine binding properties (Doyon et al., 2006 and Perry, 2006). For reasons that remain unclear, we did not detect Spt16, a mammalian FACT (facilitates chromatin transcription) complex member, shown previously to interact with the carboxyl terminus of Sas3, nor did we detect any of the other ribonuclear polypeptides isolated in the initial NuA3 characterization (John et al., 2000).

We also purified NuA3 from a genomically tagged Yng1 point mutant (W180E), predicted by our alignment between the Yng1 plant homeodomain (PHD) finger and the second PHD finger in BPTF to ablate interaction with H3K4me3 (Li et al., 2006 and Wysocka et al., 2006). Importantly for the interpretation of studies presented below, this point mutant yielded an intact NuA3 complex, with a highly similar, if not identical, subunit composition to wild-type Yng1 (data not shown).

Intact PHD Finger of Yng1 is Required for NuA3 Association with H3 K4me3

Multisubunit complexes in which HATs typically exist in vivo serve to enhance the specificity of the HATs for their histone or chromatin substrates (Eberharter et al., 1998, Grant et al., 1997 and Sendra et al., 2000). To address whether the NuA3 complex can specifically bind methylated K4, we tested the ability of H3 histone peptides with different methyl states to pull down genomically tagged NuA3 members from cellular extracts. Members of the NuA3 complex were TAP tagged and extracted as above. These extracts were then incubated with biotinylated H3 peptides bearing unmodified, mono-, di-, or trimethylated K4. Associated proteins were pulled down with streptavidin resin, resolved by SDS-PAGE, and visualized with antibodies against the PrA epitope. We observed that the NuA3 members Yng1, Sas3, Nto1, and Eaf6 were enriched in the trimethylated K4 peptide pull-down, as compared to unmodified, monomethyl, and dimethyl K4 peptides (FIGS. 2Aa-2Ac and 2Ae), suggesting that NuA3 displays a preference for H3K4me3. Swd3, a homolog of WDR5, was tested in this assay as a potential H3K4me2 effector (Flanagan et al., 2005 and Wysocka et al., 2005) but did not detectably interact with H3 peptides (FIG. 2Af).

To confirm that the interaction detected in FIG. 2A was specific for H3K4me3 (H3 polypeptide trimethylated on lysine 4), we performed pull-downs with additional trimethylated histone peptides. Since we were unable to detect significant enrichment with trimethylated peptides other than H3K4me3 (FIG. 2Ba), we conclude that NuA3 interaction with H3K4me3 also required the K4 proximal sequence. In contrast, Yng1 W180E protein was not pulled down with any trimethylated histone peptide (FIG. 2Bb), including H3K4me3, suggesting that the interaction of Yng1 with H3K4me3 is solely directed through the PHD finger.

Given that NuA3 contains several proteins besides Yng1 with potential chromatin-interacting modules, the association of NuA3 with trimethylated K4 peptide could be partially mediated by another complex member (i.e., Nto1 contains two PHD fingers in tandem). Therefore, we performed pull-downs in Yng1-tagged strains deleted for various complex members. As expected, a positive control, consisting of tagged Yng1 reintroduced into an YNG1 knockout, was enriched in the trimethyl K4 pull-down (FIG. 2Ca). Furthermore the W180E mutant was not enriched in any pull-down (FIG. 2Cb), suggesting the complete ablation of H3K4me3 binding in this mutant. A pull-down with a strain expressing a genomic copy of protein A alone served as a negative control (FIG. 2Cf). As shown in (FIGS. 2Cc and 2Cd), the interaction between Yng1 and H3K4me3 remains robust in preparations from strains missing the Nto1 and Sas3 NuA3 components, suggesting that Yng1 binding to H3K4me3 is direct. Moreover, the binding of Yng1 to H3K4me3 in extracts from strains deleted for Swd3 (FIG. 2Ce) also remained intact, suggesting that this protein linked to H3K4me2 is not contributing to the NuA3-H3K4me3 interaction. These data suggest that the NuA3 complex binds to H3K4 directly through an interaction between Yng1 and H3K4me3 and that this specificity is likely dictated through the Yng1 PHD finger.

The Interaction of the Yng1 PHD Finger with K4me3 Enhances NuA3 HAT Activity on Histone H3 Substrates Our demonstration that the Yng1 PHD finger preferentially binds K4me3, raised the intriguing possibility that NuA3 HAT activity may be increased on K4me3 peptides substrates. If correct, this finding would serve to provide a molecular explanation for why both hyperacetylation and K4me3 have been linked on the same H3 tail (Zhang et al., 2004). The HAT activity of purified NuA3 was therefore assayed using H3 histone peptides methylated to different degrees at K4. The peptides have SEQ ID NO:1 (ARTKQTARKSTGGKAPRKQLYK) with biotin attached at the C-terminus and K4 trimethylated). As shown in FIG. 3A, K4me3 peptide was consistently a better substrate for acetylation by NuA3 relative to di-, mono-, and unmethylated peptides. Since we demonstrated that the W180E point mutant abrogates Yng1 binding to K4me3, we reasoned that the NuA3 purified from W180E strains would no longer show higher activity in trimethylated peptides. Indeed, the activity of the W180E NuA3 was significantly reduced in K4 trimethylated peptides versus the unmodified controls.

Mass Spectrometry to Identify the Number and Location of Added Acetyl Groups to Histone H3 Peptide Substrates.

To further test the substrate preference of our NuA3 preparation, H3 peptides preacetylated either on K14 alone or dually on K9/K14 (FIG. 3A) were used in NuA3 acetylation assays. Consistent with previous characterizations for NuA3 enriched fractions (Eberharter et al., 1998), NuA3 could not appreciably acetylate peptides already preacetylated on K14. These data suggested that K14 was the preferred site of NuA3 activity on the N-terminal tail of histone H3, an observation reinforced by a previous study in which H3K14 was identified as a major site of acetylation on a nucleosomal substrate (Howe et al., 2001). In order to further determine the amount and position of acetylation detected in FIG. 3A for the trimethylated K4 peptide, Yng1-TAP-containing NuA3 protein complex was incubated with trimethylated K4 peptide and acetyl coenzyme A, and reaction products were analyzed by mass spectrometry (Tackett et al., 2005b). The mass spectrum of this reaction showed that only a single acetylation was detectable for the H3K4me3 N-terminal peptide (FIG. 3B). Tandem mass spectrometric analysis of this sample revealed that this single acetylation is primarily on K14, with acetylations at K9 and K18 detected at levels barely above background (FIG. 3C). The demonstration that our tagged Yng1 containing NuA3 complex catalyzes preferential acetylation of K14 when K4 is trimethylated supports our HAT assays performed with preacetylated H3K14ac peptide in FIG. 3A. Therefore, our data are most consistent with the idea that K4me3 increases H3K14 acetylation activity of NuA3, likely through increased affinity of the HAT complex via the PHD finger on Yng1.

Discussion

Trimethylation of H3K4 and increased acetylation on H3 are strongly associated with promoter and 5' regions of actively transcribing genes (Pokholok et al. 2005 and references within). For example, a strong correlation has been observed between H3K4me and H3 hyperacetylation at MLL target genes (Milne et al., 2005) and at c-fos and c-jun (Hazzalin and Mahadevan, 2005).

Here, we have demonstrated that an intact Yng1 PHD finger enhances K14-specific NuA3 HAT activity on H3K4me3 peptides. A biotin-labeled peptide fragment of H3 was used as substrate for the NuA3 HAT complex. After enzymatic acetylation, the peptide substrate was fully acetylated with perdeuterated acetic anhydride to create chemically identical peptides for mass spectrometric analysis. The chemically identical fully acetylated peptides differ in the isotopic composition of the added acetyl groups depending on whether the acetyl group was added by enzymatic action or synthetically. Since the fully acetylated peptides are chemically identical they fragment identically in mass spectrometry, which facilitates analysis by mass spectrometry to identify the positions of enzymatically added acetyl groups and the percent of the peptide population acetylated at each lysine residue. It was found that only one lysine residue of the peptide was significantly acetylated by the NuA3 HAT—lysine 14.

REFERENCES CITED

Berger S L (2002) Histone modifications in transcriptional regulation. Curr Opin Genet Dev. 12(2):142-148.

Bienz, M. (2006) The PHD finger, a nuclear protein-interaction domain, Trends Biochem. Sci. 31: 35-40.

Cheung W L, Briggs S D, Allis C D (2000) Acetylation and chromosomal functions. Curr Opin Cell Biol. 2000 June; 12(3):326-33.

Doyon, Y., W. Selleck, W. S. Lane, S. Tan and J. Cote (2004) Structural and functional conservation of the NuA4 histone acetyl transferase complex from yeast to humans. Mol. Cell. Biol. 24: 1884-1896.

Eberharter, A., S. John, P. A. Grant, R. T. Utley and J. L. Workman (1998) Identification and analysis of yeast nucleosomal histone acetyl transferase complexes. Methods 15: 315-321.

Espada J, Ballestar E, Fraga M F, Villar-Garea A, Juaranz A, Stockert J C, Robertson K D, Fuks F, Esteller M. (2004) Human DNA methyltransferase 1 is required for maintenance of the histone H3 modification pattern. J Biol Chem. 279(35):37175-84.

Flanagan, J. F., L. Z. Mi, M. Chruszcz, M. Cymborowski, K. L. Clines, Y. Kim, W. Minor, F. Rastinejad and S. Khorasanizadeh (2005) Double chromodomains cooperate to recognize the methylated histone H3 tail. Nature 438: 1181-1185.

Gilbert N, Thomson I, Boyle S, Allan J, Ramsahoye B, Bickmore W A. (2007) DNA methylation affects nuclear organization, histone modifications, and linker histone binding but not chromatin compaction. J Cell Biol. 2007 May 7; 177(3):401-11.

Glaser K B, Staver M J, Waring J F, Stender J, Ulrich R G, Davidsen S K. (2003) Gene expression profiling of multiple histone deacetylase (HDAC) inhibitors: defining a common gene set produced by HDAC inhibition in T24 and MDA carcinoma cell lines. Mol Cancer Ther 2(2):151-163.

Grant, P. A., L. Duggan, J. Cote, S. M. Roberts, J. E. Brownell, R. Candau, R. Ohba, T. Owen-Hughes, C. D. Allis and F. Winston et al. (1997) Yeast Gcn5 functions in two multisubunit complexes to acetylate nucleosomal histones: characterization of an Ada complex and the SAGA (Spt/Ada) complex. Genes Dev. 11: 1640-1650.

Grignani, F., Dematteis, S., Nervi, C., Tomassoni, L., Gelmetti, V., Cioce, M., Fanelli, M., Ruthardt, M., Ferrara, F., Zamir, I., Seiser, C., Lazar, M., Minucci, S., and Pelicci, P. (1998) Fusion proteins of the retinoic acid receptor-α recruit histone deacetylase in promyelocytic leukemia. Nature (Lond.) 391:815-818.

Hazzalin, C. A. and L. C. Mahadevan (2005) Dynamic acetylation of all lysine 4-methylated histone H3 in the mouse nucleus: analysis at c-fos and c-jun. PLoS Biol. 3: e393.

Howe, L., D. Auston, P. Grant, S. John, R. G. Cook, J. L. Workman and L. Pillus (2001) Histone H3 specific acetyl transferases are essential for cell cycle progression. Genes Dev. 15: 3144-3154.

Howe, L., T. Kusch, N. Muster, R. Chaterji, J. R. Yates 3rd and J. L. Workman (2002) Yng1p modulates the activity of Sas3p as a component of the yeast NuA3 histone acetyl transferase complex. Mol. Cell. Biol. 22: 5047-5053.

Jenuwein and Allis, (2001) T. Jenuwein and C. D. Allis, Translating the histone code. Science 293: 1074-1080.

John, S., L. Howe, S. T. Tafrov, P. A. Grant, R. Sternglanz and J. L. Workman (2000) The something about silencing protein, Sas3, is the catalytic subunit of NuA3, a yTAF(II)30-containing HAT complex that interacts with the Spt16 subunit of the yeast CP (Cdc68/Pob3)-FACT complex. Genes Dev. 14: 1196-1208.

Kabani, M. Kabani, K. Michot, C. Boschiero and M. Werner (2005) Anc1 interacts with the catalytic subunits of the general transcription factors TFIID and TFIIF, the chromatin remodeling complexes RSC and INO80, and the histone acetyl transferase complex NuA3, Biochem. Biophys. Res. Commun. 332: 398-403.

Kimura A, Matsubara K, Horikoshi M. (2005) A decade of histone acetylation: marking eukaryotic chromosomes with specific codes. J Biochem (Tokyo). 138(6):647-62.

Lee K K, Workman J L. (2007) Histone acetyltransferase complexes: one size doesn't fit all. Nat Rev Mol Cell Biol. 8(4):284-95.

Lin, R., Nagy, L., Inoue, S., Shao, W., Miller, W., and Evans, R. (1998) Role of histone deacetylase complex in acute promyelocytic leukemia. Nature (Lond.), 391:811-814.

Loewith, R. M. Meijer, S. P. Lees-Miller, K. Riabowol and D. Young (2000) Three yeast proteins related to the human candidate tumor suppressor p33ING1 are associated with histone acetyltransferase activities. Mol. Cell. Biol. 20: 3807-3816.

Lorincz M C, Schübeler D, Groudine M. (2001) Methylation-mediated proviral silencing is associated with MeCP2 recruitment and localized histone H3 deacetylation. Mol Cell Biol. 21(23):7913-22

McLaughlin, F et al. (2004) Histone deacetylase inhibitors open new doors in cancer therapy. Biochem Pharmacol. 68:1139-44.

Milne, T. A., Y. Dou, M. E. Martin, H. W. Brock, R. G. Roeder and J. L. Hess (2005) MLL associates specifically with a subset of transcriptionally active target genes. Proc. Natl. Acad. Sci. USA 102: 14765-14770.

Ng, H H, F. Robert, R. A. Young and K. Struhl (2003) Targeted recruitment of Set1 histone methylase by elongating Pol II provides a localized mark and memory of recent transcriptional activity. Mol. Cell 11:709-719.

Pena, P. V. F. Davrazou, X. Shi, K. L. Walter, V. V. Verkhusha, O. Gozani, R. Zhao and T. G. Kutateladze (2006) Molecular mechanism of histone H3K4me3 recognition by plant homeodomain of ING2. Nature 442: 100-103.

Perry, J. (2006) The Epc-N domain: a predicted protein-protein interaction domain found in select chromatin associated proteins. BMC Genomics 7: 6.

Pokholok, D. K., C. T. Harbison, S. Levine, M. Cole, N. M. Hannett, T. I. Lee, G. W. Bell, K. Walker, P. A. Rolfe and E. Herbolsheimer et al. (2005) Genome-wide map of nucleosome acetylation and methylation in yeast. Cell 122: 517-527.

Puig, O. et al. (2001) The tandem affinity purification (tap) method: a general procedure of protein complex purification. Methods 24, 218-229.

Qin S, Parthun M R. (2006) Recruitment of the type B histone acetyltransferase Hat1p to chromatin is linked to DNA double-strand breaks. Mol Cell Biol. 2006 May; 26(9): 3649-58.

Rigaut, G. et al. (1999) A generic protein purification method for protein complex characterization and proteome exploration. Nat. Biotechnol. 17, 1030-1032.

Santos-Rosa, H, R. Schneider, A. J. Bannister, J. Sherriff, B. E. Bernstein, N. C. Emre, S. L. Schreiber, J. Mellor and T. Kouzarides (2002) Active genes are tri-methylated at K4 of histone H3. Nature 419: 407-411.

Schneider, R., A. J. Bannister, F. A. Myers, A. W. Thorne, C. Crane-Robinson and T. Kouzarides (2004) Histone H3 lysine 4 methylation patterns in higher eukaryotic genes. Nat. Cell Biol. 6: 73-77.

Sendra, R., C. Tse and J. C. Hansen (2000) The yeast histone acetyltransferase A2 complex, but not free Gcn5p, binds stably to nucleosomal arrays. J. Biol. Chem. 275: 24928-24934.

Smith C M, Gafken P R, Zhang Z, Gottschling D E, Smith J B, Smith D L. (2003) Mass spectrometric quantification of acetylation at specific lysines within the amino-terminal tail of histone H4. Anal Biochem. 316(1):23-33.

Sterner, D. E., R. Belotserkovskaya and S. L. Berger (2002) SALSA, a variant of yeast SAGA, contains truncated Spt7, which correlates with activated transcription. Proc. Natl. Acad. Sci. USA 99: 11622-11627.

Strahl, B. D. and C. D. Allis (2000) The language of covalent histone modifications. Nature 403: 41-45.

Suzuki H, Gabrielson E, Chen W, Anbazhagan R, van Engeland M, Weijenberg M P, Herman J G, Baylin S B. (2002) A genomic screen for genes upregulated by demethylation and histone deacetylase inhibition in human colorectal cancer. Nat Genet 2002, 31(2):141-149.

Tacket, A. J. et al. (2005a) Proteomic and genomic characterization of chromatin complexes at a boundary. J. Cell Biol. 169:35-47.

Tacket, A. J. et al. (2005b) I-DIRT, a general method for distinguishing between specific and nonspecific protein interactions. J. Proteome Research 4:1752-1756.

Thiagalingam S, Cheng K H, Lee H J, Mineva N, Thiagalingam A, Ponte J F. (2003) Histone deacetylases: unique players in shaping the epigenetic histone code. Ann NY Acad Sci 983:84-100.

Turner, B M (2000) Histone acetylation and an epigenetic code. Bioessays 22: 836-845.

Workman, J L. (2006) Nucleosome displacement in transcription. Genes Devel. 20:2009-17.

Wysocka, J., T. Swigut, T. A. Milne, Y. Dou, X. Zhang, A. L. Burlingame, R. G. Roeder, A. H. Brivanlou and C. D. Allis (2005) WDR5 associates with histone H3 methylated at K4 and is essential for H3 K4 methylation and vertebrate development, Cell 121: 859-872.

Zhang, K. J. S. Siino, P. R. Jones, P. M. Yau and E. M. Bradbury (2004) A mass spectrometric "Western blot" to evaluate the correlations between histone methylation and histone acetylation, Proteomics 4: 3765-3775.

What is claimed is:

1. A kit for characterizing the activity of an acyl transferase on a substrate, the kit comprising:
   a polypeptide substrate for an acetyl transferase and/or a deacetylase, wherein the polypeptide substrate is a peptide fragment of a full-length protein; and
   an acyl-containing substance that non-enzymatically reacts with the polypeptide substrate to add acyl groups to the polypeptide substrate to generate a fully acylated polypeptide; wherein the acyl group of the acyl-containing substance differs in molecular weight from a natural isotope composition acetyl group.

2. The kit of claim 1 wherein the polypeptide substrate is a fragment of a full-length histone.

3. The kit of claim 1 wherein the acyl-containing substance that non-enzymatically reacts with the polypeptide substrate is deuterated acetic anhydride.

4. The kit of claim 1 wherein the polypeptide substrate comprises a synthetic ligand and the kit further comprises a solid substrate coupled to a receptor for the ligand.

5. The kit of claim 1 wherein the polypeptide substrate is methylated.

6. The kit of claim 1 wherein the polypeptide substrate is acetylated.

7. The kit of claim 1 wherein the kit contains two or more polypeptide substrates that differ in post-translational modifications but are identical in their amino acid sequence.

8. The kit of claim 1 further comprising acetyl-coenzyme A.

9. The kit of claim 1 wherein the polypeptide substrate is a substrate for acetylation and/or deacetylation by the acetyl transferase or deacetylase at two or more amino acid residues.

* * * * *

UNITED STATES PATENT AND TRADEMARK OFFICE
CERTIFICATE OF CORRECTION

| | |
|---|---|
| PATENT NO. | : 7,851,175 B2 |
| APPLICATION NO. | : 12/587776 |
| DATED | : December 14, 2010 |
| INVENTOR(S) | : Tackett et al. |

Page 1 of 1

It is certified that error appears in the above-identified patent and that said Letters Patent is hereby corrected as shown below:

Col. 1 line 7 insert

--Government Support
This invention was made with government support under grant P20RR015569 awarded by the United States National Institutes of Health. The government has certain rights in the invention.--

Signed and Sealed this
First Day of February, 2011

David J. Kappos
*Director of the United States Patent and Trademark Office*